United States Patent [19]
Jermyn

[11] Patent Number: 5,332,391
[45] Date of Patent: Jul. 26, 1994

[54] HOLDER FOR DENTAL HAND PIECE

[76] Inventor: Arthur C. Jermyn, 15914 Overview Rd., Poway, Calif. 92064

[21] Appl. No.: 87,452

[22] Filed: Jul. 9, 1993

[51] Int. Cl.⁵ .......................... A61C 3/02; A61C 1/02; A61C 1/08
[52] U.S. Cl. .......................................... 433/76; 433/109
[58] Field of Search ..................... 433/72, 75, 76, 109

[56] References Cited

U.S. PATENT DOCUMENTS

| | | | |
|---|---|---|---|
| 3,073,561 | 1/1963 | Jermyn | 433/76 X |
| 3,083,462 | 4/1963 | Jermyn | 433/109 |
| 4,344,755 | 8/1982 | Gold et al. | 433/76 |
| 5,017,139 | 5/1991 | Muschabac | 433/109 |

Primary Examiner—Gene Mancene
Assistant Examiner—Cindy A. Cherichetti

[57] ABSTRACT

The invention relates to a holder for a dental hand piece carrying a rotatable burr in which any one of a plurality of hand pieces, each of which has a different contra-angle, relative to the axis of the burr, can be accommodated to the same holder and coupled to the free end of a pantograph for maintaining the axis of the burr normal to the occludal plane of the teeth.

2 Claims, 1 Drawing Sheet

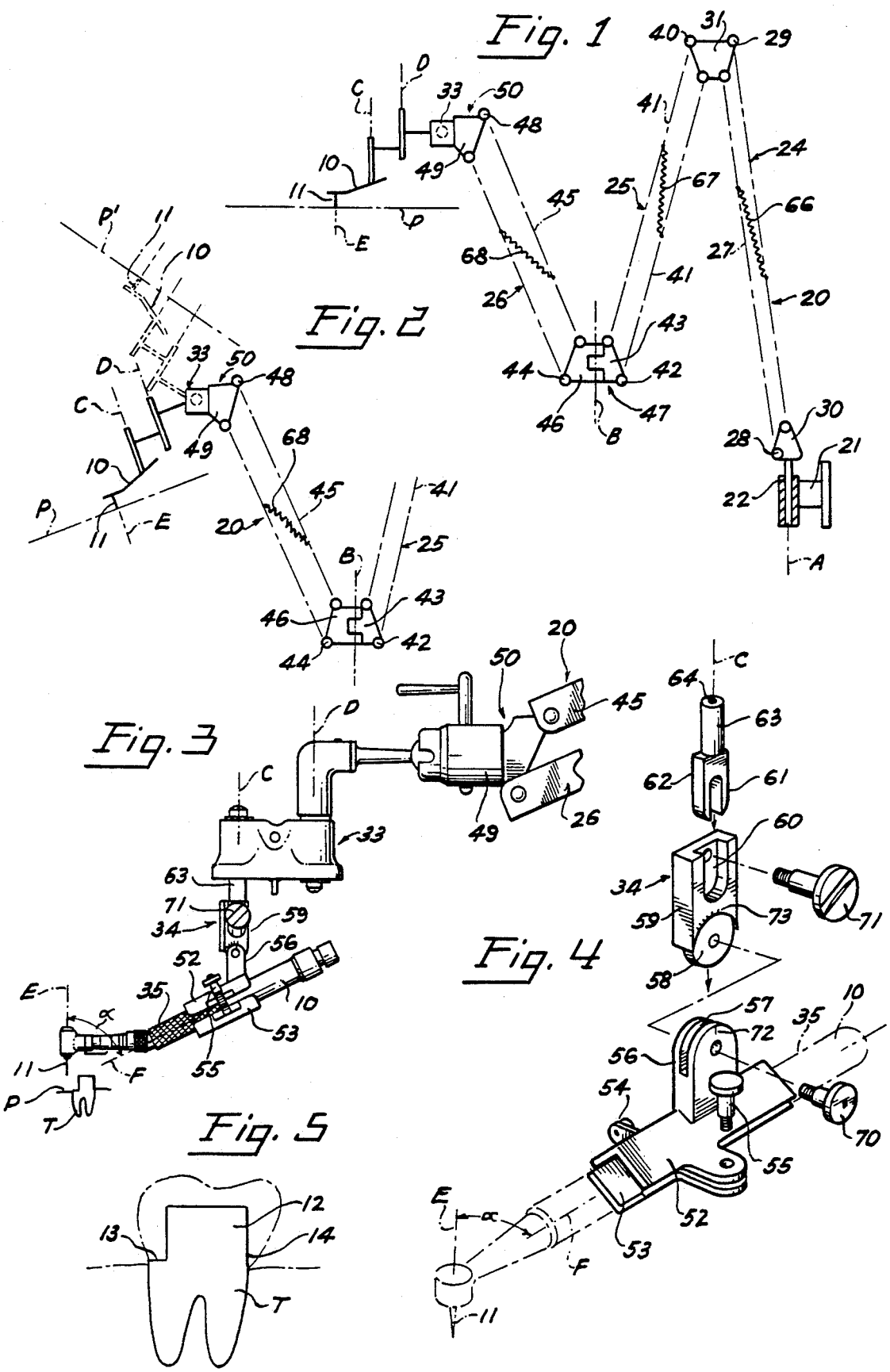

HOLDER FOR DENTAL HAND PIECE

FIELD OF THE INVENTION

The invention relates to dental apparatus and more particularly to a device mountable on the free end of a pantograph for holding any one of a plurality of dental hand pieces, each of which has a different contra-angle, and for adjusting the device to maintain the axis of a dental burr normal to the plane of occlusion of the teeth in accordance with the contra-angle of the dental hand piece being used.

DESCRIPTION OF THE ART

In the preparation of a tooth for receiving a cap or bridge, the tooth is usually cut to reduce the tooth to a substantially cylindrical shape extending to a surface near or just above the gum line. This is accomplished by utilizing a burr mounted in a dental hand piece and held by the operator, who by visual observance, attempts to cut the tooth so the cylindrical portion remaining is perpendicular to the plane of occlusion of the teeth and has a slight taper or draft to permit the cap to be readily positioned on and received by the tooth. It can be readily appreciated that such cutting of the tooth requires a great deal of skill not only in handling the hand piece but also in being able to determine the relationship between the axis of the burr and the plane of occlusion. In such a case, the burr is mounted in the contra-angle portion of the hand piece, the hand piece being driven in the usual way by a multiple link belt drive usually mounted on a standard or driven by air, if one of the newer types of hand pieces is used.

Particular reference is made to my U.S. Pat. Nos. 3,073,561 and 3,083,462 both of which relate to apparatus for maintaining the axis of a cutting element, such as a burr, normal to a predetermined plane. By means of the devices disclosed in the aforementioned patents, the operator does not need to be concerned about maintaining the position of the axis of the burr because once it has been properly set, it is always maintained in the proper position. Hence, the only concern of the operator is to direct and move the hand piece for the actual cutting of the portion of the tooth to be removed. With this arrangment, the hand piece is mounted in a device or holder separate from the normal arrangement usually employed for receiving and driving the hand piece. The hand piece is mounted in a holder or carrier which is rotatable about an angularly adjusted post and which also permits rotation of the hand piece about the axis of the holder. The holder is pivotally connected to the free end of a pantograph which, in turn, is pivotally mounted on a wall bracket or a floor pedestal. By adjusting the holder when a patient is in a position in which the plane of occlusion of the teeth can be determined, the axis of the burr is then perpendicular to this plane regardless of the direction of movement of the hand piece. The device also lends itself very readily to the cutting of a tooth in either the upper or lower jaw.

However, it has been found that a dental hand piece to be used can be any one of a number that are manufactured and each of which can have a different contra-angle. Consequently, the holder for the hand piece must be constructed in such a way so as to compensate for the difference in the contra-angle from one hand piece to another with a minimum of effort and without necessitating a holder for each hand piece in accordance with its contra-angle.

SUMMARY OF THE INVENTION

The present invention is concerned with an inter-connection between the free end of a pantograph and a holder for a dental hand piece which permits the holder to be readily and quickly adjusted for receiving a hand piece having a contra-angle different from that of the hand piece previously used. To further increase the utility of the invention, an indicia arrangement is positioned between the pantograph and the holder so as to permit the operator to set the holder at an angle that positions the burr normal to the plane of occlusion of the teeth of the patient in accordance with tile contra-angle of the hand piece. This difference in the contra-angles is apparent with the comparison of hand pieces made by different manufactures. It will be noted that the holder has to be arranged at a different angle with respect to the pantograph that is in accordance with the contra-angle of the hand piece. A fixed extension from the holder, as shown in the above patents, will only provide an adjustment for the contra-angle of the specific hand piece compatible with such holder and no other.

SUMMARY OF THE INVENTION

The primary object of the invention therefore, is to provide an interlocking arrangement between tile free end of a pantograph and a holder for a dental hand piece which permits easy exchange of hand pieces with an adjustment which will maintain the axis of the dental burr in any one of a plurality of hand pieces normal to tile plane of occlusion of the teeth irrespective of the contra-angle of tile hand piece being used.

A further object of the invention is to provide an arrangement in which indicia arranged between the free end of a pantograph and a holder for a dental hand piece permits the holder to be angularly adjusted so as to maintain the axis of the dental burr normal to the plane of occlusion of the teeth in accordance with the contra-angle of the hand piece.

Another object of the invention is to provide a holder for a dental hand piece which permits the holder to be angularly adjusted in relation to the free end of a pantograph so as to accept any one of a plurality of dental hand pieces having different contra-angles, thereby utilizing a single, inter-changeable holder.

Still another object of the invention is to provide a device mountable on the free end of a pantograph for holding a dental hand piece and which comprises a minimum number of parts and which permits the axis of a dental burr to be easily positioned and adjusted with respect to tile plane of occlusion of the teeth irrespective of the contra-angle of the dental hand piece being used.

These and other objects and advantages of the invention will be apparent to those skilled in the art by the description which follows.

DESCRIPTION OF THE DRAWING

Reference is now made to the accompanying drawing wherein like referenced numerals and characters designate like parts and wherein:

FIG. 1 is a diagrammatic view of a pantograph linkage with elements of the invention shown illustratively to disclose the axes and their relation to a horizontal plane;

FIG. 2 is a diagrammatic view similar to that of FIG. 1 and shows the axes of the elements in relation to angularly disposed planes as representative of the upper and lower jaws of a patient;

FIG. 3 is a side elevation showing the arrangement by which a dental hand piece is coupled to the free end of the pantograph linkage shown in FIG. 1;

FIG. 4 is a perspective view showing the holder for the dental hand piece and, more particularly, the arrangement by which the holder can be quickly released from the free end of pantograph linkage and also adjusted to provide for the difference, if any, in the contra-angle of the hand piece; and FIG. 5 is a vertical section through a tooth showing a cut made relative to the gum line of a shoulder on one side and a chamfer on the other side of the tooth.

DESCRIPTION OF PREFERRED EMBODIMENTS

A dental hand piece 10 of latest design can be driven by means of air or, if a conventional hand piece is used, by means of a conventional belt and pulley arrangement. In either case the hand-held hand piece is partially supported to provide the operator with means for guiding the movement of the hand piece and, hence, of the burr 11 as well, As shown in FIG. 5, tooth T is generally cut so that a central, substantially cylindrical portion 12 provides the means for receiving and securing the cap to the tooth. In such a case, the tooth is usually cut to a shoulder or chamfer 13 that is, preferably, slightly above the gum line. If such a tooth is a molar and located to the rear of the jaw, it can be readily appreciated that it is extremely difficult for tile operator to cut a cylinder which is true in every respect, that is substantially round, and tile sides 14 of which are normal to the shoulder or chamfer 13. Further, when it is necessary to cut two such teeth which may be spaced from one another to provide a bridge, the problem is still more complicated in that the axes of both cylindrical portions must be and should be parallel to provide the best fit for the bridge. Also, in the event two such teeth are not in the same plane of occlusion, then the possibility of cutting the portions 12 so that their respective axes are parallel is extremely remote. The same problem exists for the preparation of a tooth to receive an inlay for which the device described herein can also be used.

To overcome the difficulties mentioned hereinabove and to insure that all cuts that are made by the operator are normal to the established plane of occlusion of the teeth, the device, or pantograph structure designated broadly by the numeral 20 in FIGS. 1 and 2 was developed and is explained in considerable detail in my two above mentioned patents. The pantograph 20 is supported on a bracket 21 which is secured to a wall or a pedestal and is provided with a vertical post 22 on which the pantograph 20 is pivotally mounted. While the bracket or support means 21 is disclosed as a wall bracket, it is to be understood that such a support means can take the form of a floor pedestal or can be part of a standard dental unit.

Pantograph 20 comprises three sets of parallel linkages designated by the numerals 24, 25, and 26, as shown and described in more detail in the above-mentioned patents. Linkage 24 comprises two links 27 which have their respective ends 28 and 29 pivotally connected to the brackets 30 and 31, respectively. Bracket 21 is provided with a vertical bore to receive post 22 and the ends 28 of links 27 are pivotally connected to spaced lugs carried by bracket 30. The other ends 29 of links 27 are pivotally connected to bracket 31 in a similar manner. A pair of lugs on bracket 31 provide means for pivotally connecting the ends 40 of links 41 of linkage 25 thereto and the other ends 42 of links 41 are pivotally connected to the bracket 43 which forms one-half of a hinged connection 47 between the linkage 25 and the linkage 26. The linkage 26 has the ends 44 of links 45 pivotally connected to bracket 46 which forms the other half of the hinged connection 47. Ends 48 of links 45 are pivotally connected to a bracket 49. It will be noted that the links 24, 25, and 26 comprise parallel linkages and are extendable in a vertical plane passing through the axis of the post 22. The purpose of the hinged connection 47 between links 25 and 26 will be apparent from the disclosure in the above mentioned patents. In order to make pantograph 20 self-retractable, that is, to make it assume a position in which it is maintained as close to post 22 as possible, links 27 are connected by a coil tension spring 66, links 41 are connected by a spring 67, and links 45 are connected by a spring 68, as shown in FIG. 1. The aforementioned springs serves to maintain their respective links, and hence, the pantograph 20 in a retracted position until moved by the operator. These springs also provide sufficient tension to ease the pantograph to its normal or retracted position without any snap or jar which would disturb the setting of burr 11, if released by the operator when the pantograph was in an extended position. While a pantograph of the type disclosed herein comprises three pairs of linkages, it is to be understood that additional or fewer linkages may be used and that pantograph 20 may take forms other than that disclosed whereby the same result is obtained, namely, movement of burr 11 about post 22 and toward or away from said post in a vertical plane passing through the axis of post 22.

The bracket 49, in effect, comprises the free end 50 of the pantograph 20. This free end carries a housing 33 which, in turn, carries a holder 34 for the dental hand piece designated by the numeral 10. When the assembly is complete, as shown diagrammatically in FIG. 1, the pantograph 20 can be moved about axis A of post 22 and links 45 can be moved about axis B carrying the housing 33, holder 34, and the hand piece 10 therewith. Also, the entire unit can be moved toward or away from the wall on which bracket 21 is mounted, springs 66, 67, and 68, between their respective pairs of links serving to hold the entire assembly in any desired position. Housing 33 includes an axis C and an axis D which are spaced from and parallel to each other as explained more fully in my U.S. Pat. No. 3,703,561, when a particular dental hand piece is attached to the holder on the housing, the housing is then pivotally connected to the free end of the pantograph and adjusted so the axis of the burr is normal to the plane of occlusion of the teeth. The planetary gear train within the housing permits the latter to pivot relative to the free end of the pantograph with the axis of the burr remaining normal to the plane of occlusion irrespective of the direction of movement of the hand piece. The contra angle $\alpha$ which is the angle formed by the axis E of the burr 11 and the axis F of the handle portion 35 of the hand unit 10 can vary in accordance with the angle deemed most desirable by the manufacturer of the hand piece. As a result, holder 34, as described hereinafter, must be adjustably mounted with respect to housing 33 to accommodate for the angle $\alpha$ of the hand piece that is actually to be used. Normally, to set burr II so its axis E is normal to the plane of occlusion P, the housing 33 is adjusted in relation to bracket 49 and then locked in position. The pans of the unit will then assume positions, such as shown in FIG. 1. Accordingly, the axis E of burr 11 and axes C and D of housing 33 will always be parallel, and as the assembly is moved or the housing 33 is moved about axis D, the axis E will always be normal to the plane of occlusion. Also, as shown in dotted lines in FIG. 2, the housing 33, holder 34 and hand piece 10 can be rotated through 180 degrees about the center of the connection of the housing 33 to the free end 50 of the pantograph 20 to utilize burr 11 with respect to the occlusal plane P' without changing the relation of the parts. This is particularly useful when burr 11 is to be used, for example, with respect to teeth in both the upper and lower jaw.

As shown in more detail in FIG. 4, the holder 34 comprises two angular shaped members 52 and 53 which are hinged as at 54 along one edge and on the other edge by means of thumb screw 55 clamp the handle portion 35 of the hand piece 10 therebetween. Member 53 carries an upwardly projecting extension 56 which is provided with a slot 57 for receiving the flat tongue 58 on the end of an intermediate member 59. The intermediate member 59 is provided with a recess 60 which conforms in shape to the end 61 of the mounting member 62. The cylindrical portion 63 of member 62 is provided with a threaded hole 64 which, as shown in U.S. Pat. No. 3,073,561 provides the means for coupling holder 34 to housing 33.

It will be noted the mounting member 62, when coupled and secured to the intermediate member 59 by thumb screw 70 together with tongue 58 inserted and locked in slot 57 by the thumb screw 71, provides a single unit with holder 34 that is coextensive with axis C of housing 33. This assembly of elements provides a means for coupling holder 34 to the drive means associated with housing 33.

In order to accommodate a hand piece 10 that has a different contra-angle, an indicia index 72 is provided on the projection 56. An indicia scale 73 is provided on the intermediate member 59 that is oriented with respect to the index 72. The indicia scale 73 is associated with the different contra-angles of the various hand pieces 10. Hence, once a definite contra-angle has been established for a hand piece, any other hand piece having a different contra-angle can be used in holder 34 merely by replacing the hand piece, backing off thumb screw 71 and rotating holder 34 until the index 72 is aligned with the indicia associated with the hand piece to be used.

As set forth hereinabove, it can be readily appreciated by anyone skilled in the art that the invention disclosed herein provides a novel way of achieving the same result with all dental hand pieces that heretofore could not be attained because of the difference in the contra-angles of the hand pieces. There may be differences that can be effected without altering the operation, function or purpose of the invention, as described and disclosed hereinabove.

Accordingly, the invention has been described in detail with particular reference to preferred embodiments thereof, but it will be understood that variations and modifications can be effected within the spirit of the invention.

I claim:

1. A device for supporting any one of a plurality of dental hand pieces at the free end of a movable linkage, each dental hand piece having a different contra-angle relative to the rotational axis of its respective burr, and for maintaining the axis of the burr normal to the plane of occlusion of the teeth, comprising in combination:
   a holder for carrying any one of the dental hand pieces;
   a parallelogram linkage having a free end and the other end releasably supported for movement about a vertical axis and extendable in a vertical plane passing through the vertical axis;
   pivotal means detachably secured to the free end of the linkage for movement therewith to maintain constant the orientation of the axis of the burr relative to the plane of occlusion; and
   means arranged intermediate the pivotal means and the holder for coupling the holder to the pivotal means including a member releasably connected at opposite ends thereof to the pivotal means and the holder, respectively, whereby the holder is selectably releasable from the pivotal means and the member.

2. A device in accordance with claim 1 wherein the member includes angular indicia associated with an index on the holder for rectifying the angular relation of the holder relative to the pivotal means in accordance with the contra-angle of the dental hand piece carried by the holder.

* * * * *